United States Patent
Gårdhagen et al.

(10) Patent No.: US 9,110,045 B2
(45) Date of Patent: Aug. 18, 2015

(54) DEVICE FOR CONTROLLING A FLUID FLOW IN A COMPARTMENT

(71) Applicant: Envic-Sense AB, Västerås (SE)

(72) Inventors: Peter Gårdhagen, Västerås (SE); Eva-Lena Gårdhagen, Västerås (SE)

(73) Assignee: ENVIC-SENSE AB, Västerås (SE)

( * ) Notice: Subject to any disclaimer, the term of this patent is extended or adjusted under 35 U.S.C. 154(b) by 0 days.

(21) Appl. No.: 14/387,035

(22) PCT Filed: Mar. 19, 2013

(86) PCT No.: PCT/EP2013/055643
§ 371 (c)(1),
(2) Date: Sep. 22, 2014

(87) PCT Pub. No.: WO2013/139768
PCT Pub. Date: Sep. 26, 2013

(65) Prior Publication Data
US 2015/0047440 A1 Feb. 19, 2015

(30) Foreign Application Priority Data

Mar. 22, 2012 (SE) ........................... 1230030

(51) Int. Cl.
*G01N 1/00* (2006.01)
*G01N 35/08* (2006.01)
*B01L 3/00* (2006.01)
*G01N 35/10* (2006.01)

(52) U.S. Cl.
CPC ............ *G01N 35/08* (2013.01); *B01L 3/50273* (2013.01); *B01L 3/502746* (2013.01);
(Continued)

(58) Field of Classification Search
CPC .................... B01L 2300/0877; G01N 35/08
USPC .......................................................... 73/863
See application file for complete search history.

(56) References Cited

U.S. PATENT DOCUMENTS

2006/0257290 A1 11/2006 Shimizu
2009/0283456 A1 11/2009 Le Vot et al.
2011/0236262 A1 9/2011 Horii et al.

FOREIGN PATENT DOCUMENTS

WO 2005/121744 A1 12/2005

*Primary Examiner* — Hezron E Williams
*Assistant Examiner* — David Z Huang
(74) *Attorney, Agent, or Firm* — Dilworth & Barrese, LLP.

(57) ABSTRACT

The present invention relates to a device for controlling the flow of a fluid in a compartment (4) with an inlet opening (5) and an outlet opening (6). The device comprises an inlet channel (8) connected to the inlet opening for transportation of fluid to the compartment, an outlet channel (9) connected to the outlet opening for transportation of fluid from the compartment and a pump (17) arranged to pump the fluid. The compartment is provided with a third opening (12). The device comprises a distribution chamber (15) connected to the inlet channel and a third channel (14) connected between the distribution chamber and the third opening for transportation of fluid between the distribution chamber and the compartment. The pump is arranged to vary the fluid flow velocity in the distribution chamber between a lower and a higher flow velocity, and the third channel is arranged so that its transport direction depends upon the flow velocity in the distribution chamber such that the fluid in the third channel is transported in a direction from the distribution chamber to the compartment at said lower flow velocity in the distribution chamber, which leads to a slow flow in the compartment, and in the opposite direction at said higher flow velocity in the distribution chamber due an injector effect, which leads to a substantial increase in the flow velocity in the inlet channel and thus in the compartment.

10 Claims, 2 Drawing Sheets

Figure 1:
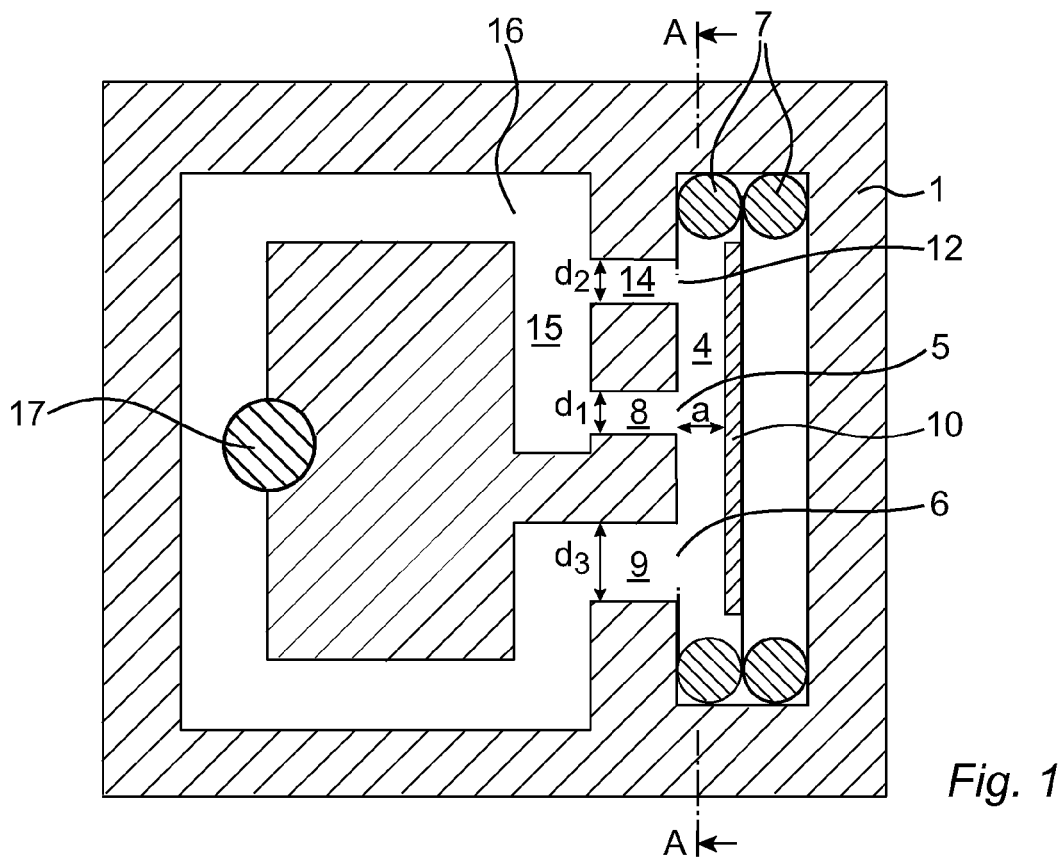

(52) U.S. Cl.
CPC .. *B01L2300/0636* (2013.01); *B01L 2300/0816* (2013.01); *B01L 2300/0877* (2013.01); *B01L 2400/0463* (2013.01); *B01L 2400/0487* (2013.01); *B01L 2400/086* (2013.01); *G01N 35/1095* (2013.01)

A-A

DEVICE FOR CONTROLLING A FLUID FLOW IN A COMPARTMENT

FIELD OF THE INVENTION

The present invention relates to a device for controlling the flow of a fluid in a compartment. The device is intended to control the flow at low volumes, in the order of less than 100 ml, and at low flow velocities, in the order of less than 100 ml/s.

PRIOR ART

There are many applications where small amounts of a fluid need to be transported, for example, in connection with various types of measurements in a fluid, such as detecting and measuring small quantities of a certain substance, counting of cells, and measurements of the kinetics of chemical reactions, and in fuel cells. Examples of substances that may need to be measured and/or detected are drugs, antibodies, viruses, DNA, RNA, nutrients, cells, and heavy metals.

WO2005/121744 shows an example of a device for detecting and measuring small quantities of a certain substance. The device comprises a measuring cell which contains a sensor and a system for transporting a fluid containing the substance to be measured past the sensor. The measuring cell comprises a measuring chamber with an inlet opening and an outlet opening, and a channel system for transporting the fluid to and from the measuring chamber. The sensor is disposed in the chamber and opposite the inlet opening of the chamber. The channel system includes an inlet channel connected to the inlet opening of the measuring chamber for transportation of the fluid to the measuring chamber, an outlet channel connected to the outlet opening of the measuring chamber for transportation of the fluid from the measuring chamber, and a pump, in the form of a friction pump, arranged to pump the fluid in the channel system.

Depending on the type of substances to be measured, sensors with different surface treatments are used. Different flow velocities are required in the measuring chamber in dependence on the sensor design and the substances to be measured. If large and heavy molecules, such as antibodies, are to be measured and the sensor surface is coated with a layer of a substance, such as a peptide, which will capture molecules, the flow velocity in the measuring chamber should be low to achieve as long dwell time as possible in the chamber, so that the antibodies have time to adhere to the sensor surface. If instead light particles, which are in a gas phase in the fluid, are to be measured, such as mercury atoms, oxygen atoms or hydrogen atoms, the particles should hit the sensor surface with a certain velocity in order to provide the particles with the energy required to detach them from the fluid and react with the coating on the sensor surface. Therefore, such applications require high flow velocities in the measuring chamber towards the sensor surface to provide particles with sufficiently high velocity so that they can reach the sensor surface and react with the coating on the sensor surface.

One way to increase the velocity of the measuring chamber is to increase the flow velocity in the inlet channel by increasing the pump speed. If the velocity in the inlet channel is increased, the pressure in the measuring chamber will also increase, which can lead to damage of the sensor and by that the sensitivity of the sensor decreases. While in some applications it is desirable to have high flow velocities near the sensor surface, it is important that the pressure in the measuring chamber is not being built up when the flow velocity increases.

Depending on what is to be detected by the sensor, an adjustment of the flow past the sensor surface is required. Today, various types of measuring cells are produced designed for different types of measurements.

There also exist other applications where it is desirable to have high flow velocities in a compartment, such as fuel cells.

OBJECT AND SUMMARY OF THE INVENTION

An object of the present invention is to provide a device which makes it possible to control the flow of a fluid in a compartment so that the flow velocity can be changed depending on the application.

Another object of the present invention is to provide a device that makes it possible to substantially increase the fluid flow velocity in a compartment without introducing an undesirable increase of the pressure in the compartment.

Another object of the present invention is to provide a device that makes it possible to achieve a higher flow velocity in the compartment than the pump is capable of giving.

These objects are achieved by a device as defined herein.

The device comprises a compartment with an inlet opening and an outlet opening, a channel system for transportation of the fluid to and from the compartment, including an inlet channel connected to the inlet opening for transportation of the fluid to the compartment, and an outlet channel connected to the outlet opening for transport of the fluid from the compartment, and a pump arranged to pump the fluid in the channel system. The device is characterized in that the compartment is provided with a third opening, and that the channel system comprises a distribution chamber connected to the inlet channel and a third channel connected between the distribution chamber and the third opening for transportation of the fluid between the distribution chamber and the compartment. The pump is arranged to vary the flow velocity in the distribution chamber between a lower and a higher flow velocity, and the third channel is arranged so that its transport direction depends upon the velocity of flow in the distribution chamber so that the fluid in the third channel is transported in a direction from the distribution chamber to the compartment at the lower flow velocity in the distribution chamber, which leads to quiet flow in the compartment, and in an opposite direction, i.e. in a direction from the compartment to the distribution chamber, at the higher flow velocity in the distribution chamber due to an injector effect, which leads to a substantially increased flow velocity in the inlet channel and thus in the compartment.

Due to the fact that the device is provided with two channels between the distribution chamber and the compartment, and the pump is arranged so that it can control the velocity of the flow in the distribution chamber, it is possible to generate various types of flows in the compartment. The invention makes it possible to alternate between a slow and a very fast flow in the compartment by just making a minor change of the pump speed.

At moderate flow velocities in the distribution chamber, the fluid in the third channel will flow in the same direction as the fluid in the inlet channel. The flow to the compartment will thus be distributed between the two channels, consequently leading to a quiet flow in the compartment. When the flow velocity increases in the distribution chamber, the static pressure in the distribution chamber will decrease relative to the static pressure in the compartment, and when the flow velocity in the distribution chamber exceeds a certain limit value, the pressure in the distribution chamber has fallen so much relative to the pressure in the compartment that the flow in the third channel changes direction, due to the so called injector effect. By that, the flow from the third channel is added to the flow that passes the inlet channel, which leads to a further increase in the flow velocity in the inlet channel, and thereby to a further increase in the flow velocity in the compartment. In this way, a larger flow velocity is achieved than what is generated by the pump. This makes it possible to use a simple and inexpensive pump and still achieve a high flow velocity.

Because the fluid flows from the compartment through the third inlet channel, the pressure decreases in the compartment even though the flow velocity in the inlet channel increases, and thus it is avoided that the pressure in the compartment builds up.

According to one embodiment of the invention, the distribution chamber is arranged to have a defined flow direction and the inlet channel and the third channel are arranged perpendicularly to the flow direction in the distribution chamber. To provide an injector effect, the flow direction in the inlet channel and the third channel should preferably be substantially perpendicular to the flow direction in the distribution chamber. However, some deviations are permissible.

In one embodiment of the invention, the third channel is parallel to the inlet channel, and the center distance between the third channel and the inlet channel lies in the range 1-2.5 mm.

In one embodiment of the invention, the difference between the cross sectional area of the inlet channel and the cross sectional area of the third channel is less than 20%. Preferably, the cross sectional areas of the inlet channel and the third channel is about the same. Due to the fact that the inlet channel and the third channel have approximately the same cross sectional area, the flow volumes of both channels are approximately equal. Since the flow direction in the third channel is opposite the flow direction in the inlet channel, an increase of the pressure in the compartment is avoided when the flow velocity in the inlet channel increases.

In one embodiment of the invention, the outlet channel has a cross sectional area that is at least 50%, and preferably 100% larger than the cross sectional area of the inlet channel. The outlet channel must have a cross sectional area substantially larger than the inlet channel to make it possible to transport away the fluid, and thereby avoid pressure build-up in the compartment.

In one embodiment of the invention, the pump is provided with speed control. The flow velocity in the distribution chamber can then be controlled in a simple manner by varying the pump speed.

Figure 2:
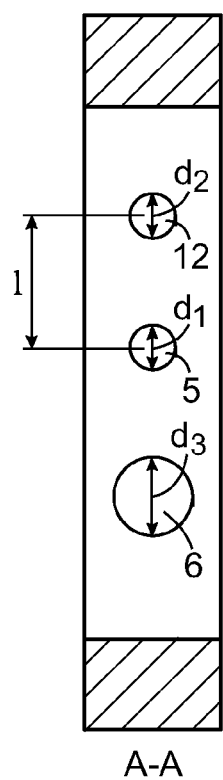

In one embodiment of the invention, the device comprises a sensor arranged opposite the inlet opening and the third opening in compartment for measuring substances in the fluid in the compartment. The third opening and the inlet channel are arranged so as to face the sensor. This embodiment makes it possible to alternate between different types of flow velocities at the sensor surface by varying the velocity of flow in the distribution chamber. A low flow velocity in the distribution chamber provides a quiet flow past the sensor surface. This allows a longer dwell time in the chamber and at the sensor for the particles to be measured. This type of flow is favorable for measuring particles that bind to a peptide, a process which takes time. A higher flow velocity in the distribution chamber leads, because of the injector effect, to a substantially increased flow velocity in the inlet channel and consequently a strong flow towards the sensor and a short dwell time of the particles in the compartment. The strong flow towards the sensor causes increased energy when the particles hit the sensor surface, thereby increasing the probability to release particles into gaseous form in the fluid, and thereby the ability to detect the particles increases. This leads to faster a measurement and increases the measure sensitivity.

The invention is very suitable for the measuring substances requiring biochemical reactions on the sensor surface.

The invention makes it possible to use the same measuring cell for measuring various types of compounds, which require various chemical reactions on the surface of the sensor. Preferably, the device is designed so that the sensor is exchangeable. Thus, it is sufficient to replace the sensor in the cell when a new type of compound is to be measured. This leads to decreased production costs and decreased costs for storage of the measuring cells.

When the flow in the third channel is flowing in a direction from the compartment to the distribution chamber, there is provided a loop due to the injector effect, which loop allows a part of the fluid containing the particles to be measured, to pass the sensor several times and thus increases the chance that the particles are measured.

In one embodiment of the invention, the distance between the inlet opening and the sensor is between 0.8and 1 mm. This embodiment ensures that the flow reaches all the way to the sensor, while a pressure build up in the compartment is avoided. To avoid build up of a pressure in the compartment, the flow resistance in the compartment should be as low as possible. In order to prevent pressure build up in the compartment, it is desirable that the distance between the inlet opening and the sensor is as large as possible. However, the larger distance between the inlet opening and the sensor, the higher flow velocity is required in the inlet channel to ensure that the flow will reach the sensor. It has been found that if the distance between the inlet opening and the sensor is between 0.8and 1 mm, is possible for the flow to reach the sensor surface with only a low pressure buildup in the compartment.

In one embodiment of the invention, the inlet opening, the outlet opening and the third opening are aligned with each other. This provides an advantageous flow past the sensor.

In one embodiment of the invention, the inlet opening is arranged between the outlet opening and the third opening. This will prevent unwanted turbulence in the compartment when the device operates under injector effect.

In one embodiment of the invention, the sensor has a measuring surface, and the inlet channel and the third channel are arranged with their longitudinal axes perpendicular to the measuring surface. Thus, the flow is directed directly towards the sensor and the flow reaches as close as possible to the measuring surface of the sensor.

BRIEF DESCRIPTION OF THE DRAWINGS

The invention will now be explained more closely by the description of different embodiments of the invention and with reference to the appended figures.

FIG. 1 shows an example of a device for controlling the flow of a fluid according to an embodiment of the invention.

FIG. 2 shows a section A-A of the device shown in FIG. 1.

FIG. 3 shows the flow to and from the sensor in the device shown in FIG. 1 when the device is operating in a first state.

FIG. 4 shows the flow to and from the sensor in the device shown in FIG. 1 when the device is operating in a second state.

FIG. 5 shows the flow to and from the sensor in the device shown in FIG. 1 when the device is operating in a third state.

DETAILED DESCRIPTION OF PREFERRED EMBODIMENTS OF THE INVENTION

FIG. 1 shows an example of a device according to the invention for controlling the flow of a fluid in a compartment.

FIG. 2 shows a cross section A-A through the device shown in FIG. 1. In this embodiment, the device is a part of a measuring cell for detecting and measuring substances in a sample. The sample is added to a fluid which is circulated in the measuring cell. The device comprises a body 1 which includes a compartment 4 in the form of an elongate measuring chamber with an inlet opening 5 for receiving the fluid containing the sample to be measured, an outlet opening 6 for the removal of the fluid after measurement, and a channel system for transportation of the fluid to and from the measuring chamber. The channel system forms a closed loop. The body 1 is preferably made of a plastic material such as polyetheretherketone (PEEK) or acrylic plastic, but can also be made of glass. The device includes a sensor 10 disposed in the measuring chamber. The sensor has a measuring surface coated with a layer of a substance, which will capture molecules of the substance to be measured. The sensor 10 is positioned along the longitudinal axis of the measuring chamber and opposite the inlet opening 5. Preferably, the measuring cell is designed so that the sensor can be replaced with another type of sensor in order to perform other types of measurements. The device comprises two seals 7, for example, in the form of O-rings to seal around the sensor.

The channel system comprises an inlet channel 8 connected to the inlet opening 5 of the measuring chamber for transport of the fluid to the measuring chamber, and an outlet channel 9 connected to the outlet opening 6 of the measuring chamber for transport of the fluid from the measuring chamber. The measuring chamber 4 is provided with a third opening 12 facing the sensor 10 . All three holes 5, 6, 12 are arranged in a line. The inlet opening 5 is provided between the outlet opening 6 and the third opening 12. The channel system comprises a third channel 14, hereinafter called injector channel, connected to the third opening 12 of the measuring chamber. The inlet channel 8, the outlet channel and the third channel 14 are arranged parallel to each other. Preferably, the inlet channel and the injector channel are arranged with their longitudinal axes perpendicular to a measuring surface of the sensor, and thus perpendicular to the longitudinal axis of the measuring chamber. The injector channel is arranged upstream of the inlet opening. In this embodiment of the invention, the inlet channel is disposed between the outlet channel and the injector channel.

If the injector channel instead is arranged between the outlet channel and the inlet channel, and the flow direction in the distribution chamber is the opposite, it would lead to a lot of turbulence in the measuring chamber when the device operates based on the injector effect. In another embodiment of the invention, there is no sensor in the compartment, and it is possible to have the outlet channel on another wall of the compartment, for example, on a side opposite to the inlet channel and the injector channel.

Figure 3:
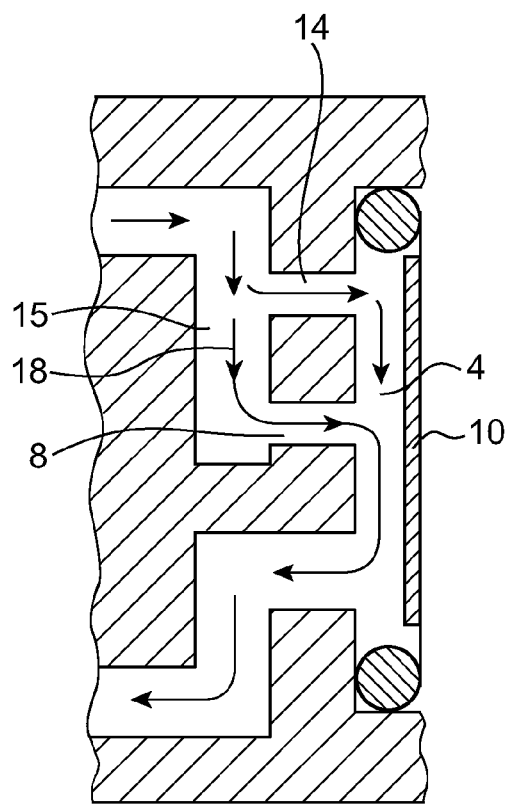

The channel system further comprises a distribution chamber 15 arranged in connection to the inlet channel 8 and the injector channel 14. The task of the distribution chamber 15 is to distribute the flow between the inlet channel 8 and the injector channel 14. The injector channel 14 is connected between the distribution chamber 15 and the third opening 12 for the transport of the fluid between the distribution chamber and the measuring chamber. The inlet channel 8 is connected between the distribution chamber 15 and the inlet opening 5 for the transport of the fluid from the distribution chamber to the measuring chamber. One end of the distribution chamber is provided with an opening 16 for receiving the fluid and the opposite end of the distribution chamber is connected to the inlet channel 8. The distribution chamber 15 is arranged so as to have a defined flow direction 18. The inlet channel 8 and the third channel 14 are arranged perpendicular to the flow direction in the distribution chamber, as shown in FIG. 3. The distribution chamber 15 is elongated and extends parallel to the measuring chamber. The inlet channel 8 and the injector channel 14 are arranged with their longitudinal axes perpendicular to the longitudinal axis of the distribution chamber.

The distance a between the inlet opening and the sensor should be less than or equal to 1 mm, preferably between 0.8 and 1 mm.

a<=1 mm

In a preferred embodiment, the inlet channel, outlet channel, and the injector channel have a circular cross section, as shown in FIG. 2. In the embodiment shown in FIGS. 1 and 2, the inlet channel 8 and the injector channel 14 have a diameter $d_1=d_2=1$ mm, and the outlet channel 9 has a diameter $d_3=1.6$ mm. It is also possible to use channels of other shapes, such as a rectangular cross section. Preferably, the cross sectional area of the inlet channel and the cross sectional area of the injector channel is equal. Preferably, the difference between the cross sectional area of the inlet channel and the cross sectional area of the injector channel should not exceed 20%. In order to prevent pressure buildup in the measuring chamber the cross sectional area of the outlet channel should be greater than the cross sectional area of the inlet channel and the injector channel. Preferably, the outlet channel has a cross sectional area which is at least 50%, and preferably at least 100% greater than the cross sectional area of the inlet channel. The center distance l between the third opening 12 and inlet opening 5 is in the range of 1-2.5 mm and are typically 2 mm.

The device includes a pump 17 arranged to pump the fluid to circulate in the channel system. The pump is, for example, a friction pump, as shown in WO2005/121744. The pump 17 is arranged so that it may vary the fluid flow velocity in the distribution chamber 15 between a lower and a higher flow velocity. Preferably, the pump is arranged so it is possible to continuously change the velocity of flow in the distribution chamber from zero up to a maximum value. In order to provide a variable flow velocity in the distribution chamber, the pump is advantageously provided with speed control. By controlling the pump speed, the flow velocity in the distribution chamber can be controlled.

The injector channel 14 is arranged so that its transport direction depends upon the flow velocity in the distribution chamber so that the fluid is transported in a direction from the distribution chamber 15 to the measuring chamber 4 at low flow velocity in the distribution chamber, which leads to a quit flow past the sensor, and in the opposite direction at a higher flow velocity in the distribution chamber due an injector effect, which leads to a substantial increase in the flow velocity in the inlet channel, and thus a strong flow towards the sensor.

The following describes how a device according to the invention may control the flow past the measuring surface of the sensor. The device may operate in three different states, which give rise to different types of flows in the measuring chamber. FIG. 3 shows the flow to and from the sensor device of FIG. 1 when operating in a first state. This state is achieved by running the pump at low or moderate speeds, which means that the flow velocity in the distribution chamber 15 varies from the low to moderate. In the first state, the fluid in the injector channel 14 flows in the same direction as in the inlet channel 8, i.e. in the direction from the distribution chamber 15 to the measuring chamber 4. This leads to a calm flow past the sensor. Thus, the sample stays a long time in the measuring chamber. This is, for example, advantageous for measuring of substances requiring a long time to react with the coating on the sensor surface. This type of flow is, for example, favorable for measuring particles, such as arsenic, which binds to a peptide, which is a process that takes time.

Figure 4:
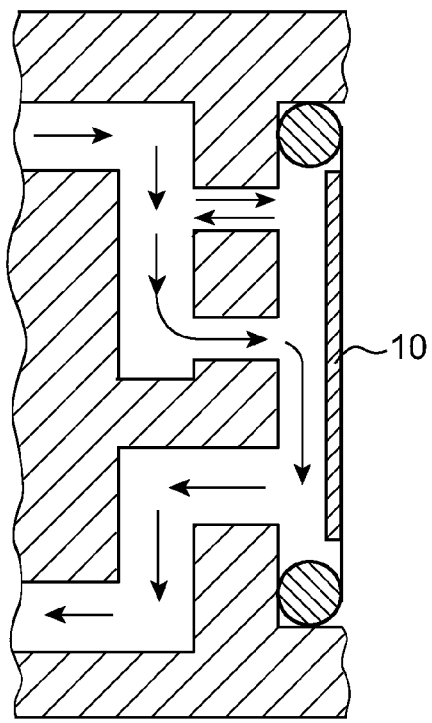

FIG. 4 shows the flow to and from the sensor when the device is operating in a second state. When the pump speed is increased, the flow velocity in the distribution chamber will increase. When the flow velocity in the distribution chamber increases, the static pressure in the distribution chamber decreases relative to the static pressure in the measuring chamber. When the flow velocity in the distribution chamber reaches a critical velocity, the pressure in the distribution chamber will be the same as in the measuring chamber, which leads to that the flow in the injector channel is stopped and all transport of the fluid from the distribution chamber to the measuring chamber occurs via the inlet channel. The device works now in its second state.

Figure 5:
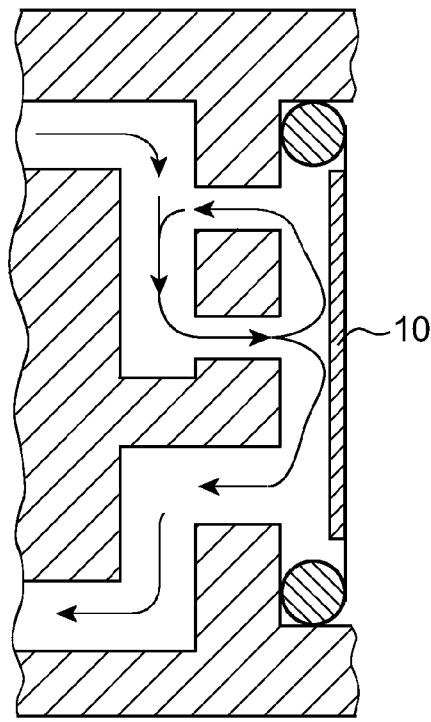

If the pump speed is further increased, and thus the flow velocity in the distribution chamber is further increased, the static pressure in the distribution chamber decrease relative to the static pressure in the measuring chamber, so that the pressure in the distribution chamber is less than the pressure in the measuring chamber, causing the flow of the injector channel to change direction due to the injector effect. The device now operates in its third state, as shown in FIG. 5. In this state, the fluid in the injector channel flows from the measuring chamber to the distribution chamber, while the fluid in the inlet channel flows from the distribution chamber to the measuring chamber.

The fact that the fluid flows from the measuring chamber to the distribution chamber leads to an increased volume of the fluid in the distribution chamber.

Since a fluid, such as water, can not be compressed, this causes a sharp increase in the flow velocity in the inlet channel. This means that the flow from the injector channel is added to the flow in the inlet channel. In this way, a larger flow is achieved in the inlet channel than the pump itself is able to generate. The high flow velocity in the inlet channel enables the fluid flow to reaches all the way to the sensor surface, as shown in FIG. 5. The strong flow at the sensor causes the particles in the fluid to be thrown against the sensor surface with a certain force, which gives the particles the energy required to detach them from the fluid and react with the coating on the sensor surface, thereby increasing the ability to detect the particles. A higher flow velocity in the distribution chamber will thus lead to a significantly increased flow velocity in the inlet channel and consequently a strong flow towards the sensor and a short dwell time for the particles in the measuring chamber. This is, for example, advantageous for the measurement of light particles in gas phase in the fluid, such as mercury atoms, oxygen atoms or hydrogen atoms.

As shown in FIG. 5, the third channel 14 and the inlet channel 8 form a loop that allows a part of the fluid to pass past the sensor multiple times, thus increasing the chances that the sensor detects particles.

By replacing the sensor in the measuring cell and changing the pump speed, the same measuring cell can be used for different types of measurements.

The present invention is not limited to the embodiment shown, but can be varied and modified within the scope of the appended claims. For example, the compartment need not include any sensor. Furthermore, the length of the measuring chamber and the distribution chamber may vary. The size of the device can obviously vary depending on the size of the volumes of the fluid which has to pass through the compartment. Thanks to its simple design, it is easy to change the size of the device and to design it for flows of different volume sizes. It is possible to scale down the device so that it is able to control the flow of the order of µl/s.

The invention claimed is:

1. A device for controlling the flow of a fluid in a compartment with an inlet opening and an outlet opening, wherein the device comprises:
   a channel system for transportation of fluid to and from the compartment, including an inlet channel connected to the inlet opening for transportation of fluid to the compartment, and an outlet channel connected to the outlet opening for transport of fluid from the compartment, and
   a pump arranged to pump the fluid in the channel system, wherein
      the compartment is provided with a third opening, the channel system comprises a distribution chamber connected to the inlet channel, and a third channel connected between the distribution chamber and said third opening for transportation of fluid between the distribution chamber and the compartment, and the pump is arranged to vary the flow velocity in the distribution chamber between a lower and a higher flow velocity, and the third channel is arranged so that its transport direction depends upon the flow velocity in the distribution chamber such that the fluid in the third channel is transported in a direction from the distribution chamber to the compartment at said lower flow velocity in the distribution chamber, which leads to a slow flow in the compartment, and the fluid in the third channel is transported in the opposite direction at said higher flow velocity in the distribution chamber due an injector effect, which leads to a substantial increase in the flow velocity in the inlet channel and thus in the compartment.

2. The device according to claim 1, wherein the distribution chamber is arranged so that it has a defined flow direction, and the inlet channel and the third channel are arranged perpendicular to the flow direction in the distribution chamber.

3. The device according to claim 1, wherein the third channel is parallel to the inlet channel and the center distance between the third channel and the inlet channel lies in the range of 1-2.5 mm.

4. The device according to claim 1, wherein the difference between the cross sectional area of the inlet channel and the cross sectional area of the third channel is less than 20%.

5. The device according to claim 1, wherein the outlet channel has a cross sectional area that is at least 50%, preferably 100% larger than the cross sectional area of the inlet channel.

6. The device according to claim 1, wherein the inlet opening, the outlet opening and the third opening are arranged in line with each other, and the inlet opening is arranged between the outlet opening and the third opening.

7. The device according to claim 1, wherein the device comprises a sensor disposed opposite the inlet opening and the third opening in the compartment, for measuring substances in the fluid in the compartment.

8. The device according to claim 7, wherein the sensor has a measuring surface, and the inlet channel and the third channel are arranged with their longitudinal axes perpendicular to the measuring surface of the sensor.

9. The device according to claim 7, wherein the distance between the inlet opening and the sensor surface is between 0.8 and 1 mm.

10. The device according to claim 7, wherein the device is designed so that the sensor is exchangeable.

* * * * *